United States Patent
Wada

[11] Patent Number: 5,833,679
[45] Date of Patent: Nov. 10, 1998

[54] ABSORBENT STRUCTURE OF SANITARY ARTICLE

[75] Inventor: Ichiro Wada, Kawanoe, Japan

[73] Assignee: Uni-Charm Corporation, Ehime-ken, Japan

[21] Appl. No.: 746,805

[22] Filed: Nov. 18, 1996

Related U.S. Application Data

[63] Continuation of Ser. No. 522,438, Aug. 31, 1995, abandoned.

[30] Foreign Application Priority Data

Sep. 1, 1994 [JP] Japan .................................... 6-208780

[51] Int. Cl.$^6$ .............................. A61F 13/15; A61F 13/20
[52] U.S. Cl. ......................... 604/384; 604/378; 604/366; 604/385.1; 604/358
[58] Field of Search ..................... 604/358, 365, 604/366, 370, 378–380, 384, 385.1

[56] References Cited

U.S. PATENT DOCUMENTS

| | | | |
|---|---|---|---|
| 3,065,751 | 11/1962 | Gobbo, Sr. et al. | 604/379 |
| 3,345,243 | 10/1967 | Kalaites | 604/366 |
| 3,766,922 | 10/1973 | Krusko | 604/380 |
| 3,881,490 | 5/1975 | Whitehead et al. | 604/366 |
| 3,886,941 | 6/1975 | Duane et al. | 604/366 |
| 4,059,114 | 11/1977 | Richards | 604/366 |
| 4,333,979 | 6/1982 | Sciaraffa et al. | 604/366 |
| 4,443,512 | 4/1984 | Delvaux | 604/379 |
| 4,463,045 | 7/1984 | Ahr et al. | 428/131 |
| 4,505,705 | 3/1985 | Matthews et al. | 604/366 |
| 4,591,523 | 5/1986 | Thompson | 428/131 |
| 4,624,666 | 11/1986 | Derossett et al. | 604/366 |
| 4,629,643 | 12/1986 | Curro et al. | 428/131 |
| 4,678,464 | 7/1987 | Holtman | 604/379 |
| 4,781,710 | 11/1988 | Megison et al. | 604/378 |
| 5,078,710 | 1/1992 | Suda et al. | 604/366 |
| 5,128,193 | 7/1992 | Anapol et al. | 604/379 |
| 5,383,870 | 1/1995 | Takai et al. | 604/366 |
| 5,514,105 | 5/1996 | Goodman, Jr. et al. | 604/385.1 |
| 5,613,960 | 3/1997 | Mizutani | 604/366 |

FOREIGN PATENT DOCUMENTS

| | | | |
|---|---|---|---|
| 6-190002 | 7/1994 | Japan | 604/366 |
| 6-190003 | 7/1994 | Japan | 604/366 |

*Primary Examiner*—Mickey Yu
*Assistant Examiner*—Francis K. Cuddihy
*Attorney, Agent, or Firm*—Lowe Hauptman Gopstein Gilman & Berner

[57] ABSTRACT

A sanitary napkin includes a liquid-permeable topsheet made of thermoplastic synthetic fibers and a liquid-absorbent core integrated with the topsheet at debossed spots. The debossed spots are formed as enlarged diameter upper depressions formed by compressing the topsheet and core together, and reduced diameter lower depressions formed by partially heating the bottom of the depression while under pressure, resulting in the heat-sealing of the topsheet and the core.

10 Claims, 2 Drawing Sheets

ABSORBENT STRUCTURE OF SANITARY ARTICLE

This application is a continuation of U.S. application Ser. No. 08/522,438 filed Aug. 31,1995, now abandoned.

BACKGROUND OF THE INVENTION

The present invention relates to an absorbent structure for sanitary articles such as sanitary napkins, disposable diapers or mother's milk absorbent pads generally used to absorb body fluids.

Conventional absorbent structures for sanitary articles generally comprise a liquid-absorbent core and a liquid-permeable sheet with which at least one surface of the core is covered. Such a core usually has the other surface covered with a liquid-impermeable sheet in order to prevent the quantity of body fluids once absorbed by the core from leaking.

For such sanitary articles, the liquid-permeable sheet and the liquid-absorbent core are preferably put in tight contact with each other so that a quantity of body fluids flowing therebetween may be rapidly transferred from the liquid-permeable sheet to the liquid-absorbent core under the capillary action.

Particularly with the sanitary articles using a nonwoven fabric made of thermoplastic synthetic fibers as a topsheet which contacts the wearer's skin, the body fluids will not be absorbed by the core but flow over the surface of the nonwoven fabric, possibly resulting in sideways leakage unless the topsheet is in tight contact with the core, since such nonwoven fabric practically has no liquid holding ability.

FIG. 3 is a fragmentary sectional view of an absorbent structure for sanitary napkin subjected to thermal debossing of prior art. Referring to FIG. 3, this absorbent structure 30 comprises a liquid-permeable topsheet 33 made by a nonwoven fabric of thermoplastic synthetic fibers, a liquid-impermeable backsheet 34 made of a synthetic resin film and a liquid-absorbent core 35 disposed between these two sheets 33, 34, and has a total thickness "t". At the respective thermally debossed spots, the topsheet 33 forms depressions 36 each having a depth of ½ "t" or larger with respect to the total thickness "t" of the absorbent structure 30 and, at portion 37 of each depression 36 and adjacent this as indicated by hatching, the individual fibers of the topsheet 33 are molten and welded to the core 35. While each depression 36 of the topsheet 33 preferably has a depth of ½ "t" or larger in order to achieve a reliably tight contact between the topsheet 33 and the core 35, the deeper the depression 36 is, the larger the upper opening diameter "d" is.

With such absorbent structure 30, most of menstrual discharge permeates through the topsheet into the core 35 at a continuous planar region defined around the respective depressions 33 so as to be substantially concealed under the topsheet 33. However, at the respective depressions 33, the filmy portions prevent a remaining quantity of menstrual discharge from penetrating through the topsheet and thus the discharge remains in these depressions 36. Consequently, such known absorbent structure 30 is disadvantageous in that the quantity of menstrual discharge staying in the depressions maintains the top surface of the topsheet in wet condition during its use, deteriorating the feeling of comfort by the wearer, and makes menstrual discharge uncomfortably visible for wearer when she disposes the used article.

Accordingly, it is a principal object of the invention to solve the problem as mentioned above by providing an improved arrangement such that each of the debossed spots at which a liquid-permeable topsheet is intermittently integrated with a liquid-absorbent core comprises a diameter upper depression formed by compressing the sheet and core together and a reduced diameter lower depression lying inside the enlarged diameter upper depression and formed by partially heat-sealing the topsheet defining a bottom of the enlarged diameter upper depression to the core under a pressure.

SUMMARY OF THE INVENTION

The object set forth above is achieved, in accordance with the invention, by an absorbent structure for sanitary article at least comprising a liquid-absorbent core and a liquid-permeable topsheet made of thermoplastic synthetic fibers with which at least one surface of the core is covered, the core and the topsheet being integrated with each other at a plurality of independently and intermittently distributed debossed spots, wherein the improvement including each of the debossed spots comprises an enlarged diameter upper depression formed by partially compressing the core and the topsheet together in the direction of thickness and a reduced diameter lower depression lying inside the enlarged diameter upper depression and formed by partially depressing a bottom of the enlarged diameter upper depression further in the direction of thickness and heat-sealing this additionally depressed portion of the bottom of the enlarged diameter upper depression to the core.

With the absorbent structure for sanitary article arranged as described above, the respective enlarged diameter upper depressions formed by debossing, i.e., compressing the core and the topsheet in the direction of thickness, are thinner than the remainder having been subjected to no debossing. On the other hand, the respective reduced diameter lower depressions lying inside the associated enlarged diameter upper depression can be formed to be relatively shallow so that, even if the depression wall is filmy, a quantity of body fluids possibly staying therein can be sufficiently decreased to alleviate the feeling of wetness which is uncomfortable to the wearer of this sanitary article. When the wearer disposes the sanitary article after use, the body fluids staying in the respective diameter reduced lower depressions is practically inconspicuous.

PREFERRED EMBODIMENTS OF THE INVENTION

Figure 1:
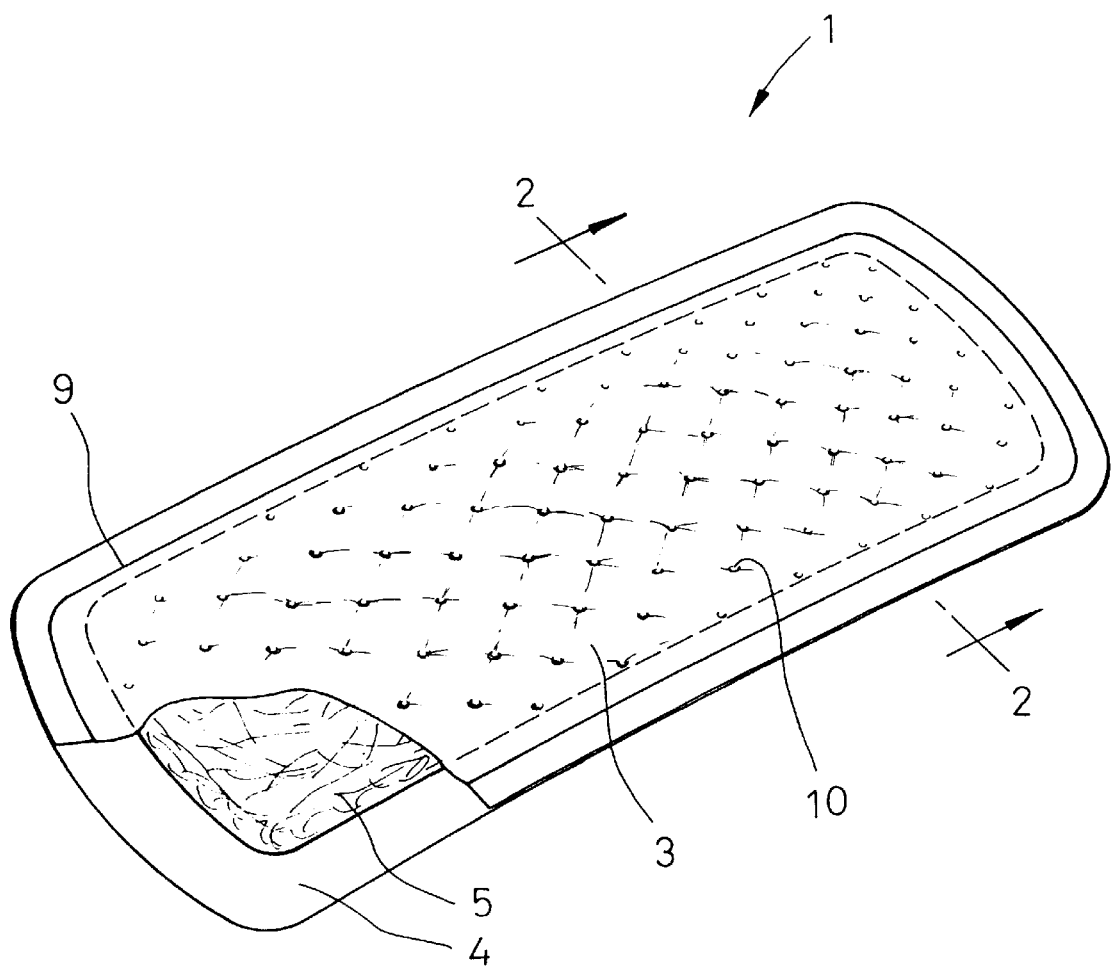
FIG. 1 is a perspective view of a sanitary napkin as a specific embodiment of the invention, as partially broken away.

Referring to FIG. 1, a sanitary napkin 1 comprises a liquid-permeable topsheet 3, a liquid-impermeable backsheet 4 and a liquid-absorbent core 5 disposed between these two sheets 3, 4 which have, in turn, their portions extending outwardly beyond a peripheral edge of the core 5 bonded together along a sealing line 9. The topsheet 3 is made of a nonwoven fabric of thermoplastic synthetic fibers and formed on its top surface with a plurality of debossed spots 10 sunken toward the core 5. The backsheet 4 is made of a thermoplastic synthetic resin film. The core 5 is generally molded from liquid-absorbent material such as fluff pulp or a mixture of fluff pulp and hightly water absorptive polymer powders, and thermoplastic synthetic fibers up to 20% by weight may be mixed into the liquid-absorbent material to improve its moldability and heat-sealability with respect to the topsheet 3.

Figure 2:
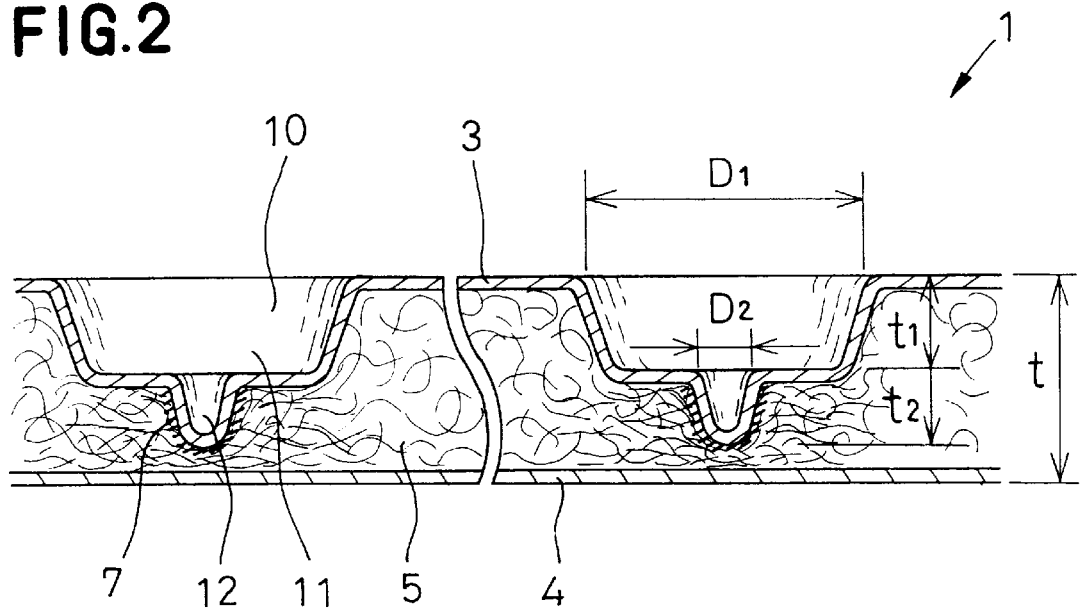
FIG. 2 is a sectional view taken along a line 2—2 in FIG. 1, showing an important part of the sanitary napkin arranged according to the invention in an enlarged scale.

Referring to FIG. 2, the napkin 1 has a thickness "t" and each of the debossed spots 10 comprises an enlarged diameter upper depression 11 with its opening having a diameter $D_1$ and a depth $t_1$, and a reduced diameter lower depression 12 with its opening having a diameter $D_2$ and a depth $t_2$. The enlarged diameter upper depression 11 is formed by compressing the napkin 1 from the topsheet 3 toward the backsheet 4 and the reduced diameter lower depression 12 is formed by compressing a bottom of the enlarged diameter upper depression 11 under a pressure, i.e., by thermally debossing the bottom. In the enlarged diameter upper depression 11, the individual synthetic fibers of the topsheet 3 constituting the enlarged diameter upper depression 11 are mechanically intertwined with the individual fibers of the core 5 during the compression and, in the reduced diameter lower depression 12, a peripheral wall formed by the topsheet 3 is filmily molten by a sphere as indicated by hatching 7 and heat-sealed to the core 5. The debossed spots are preferably formed so as to have an area ratio of 5 to 25% with respect to the total area of the topsheet 3 and the opening diameters $D_1$, $D_2$ are preferably 1 to 15 mm and 0.5 to 3 mm, respectively. It should be understood that a configuration of the debossed spot 10 as viewed from above is not limited to a circle and the opening diameters $D_1$, $D_2$ should be understood to be the maximum diameters of the upper and lower depressions, respectively. The depths $t_1$, and $t_2$ of the upper and lower depressions are preferably selected so that each of them corresponds to 20% or more and $t_1+t_2$ corresponds to 50% or more with respect to the thickness "t" of the napkin 1. An arrangement is also possible such that $t_1+t_2$="t" and a lower end of the reduced diameter lower depression reaches the backsheet 4 and is heat-sealed thereto.

Figure 3:
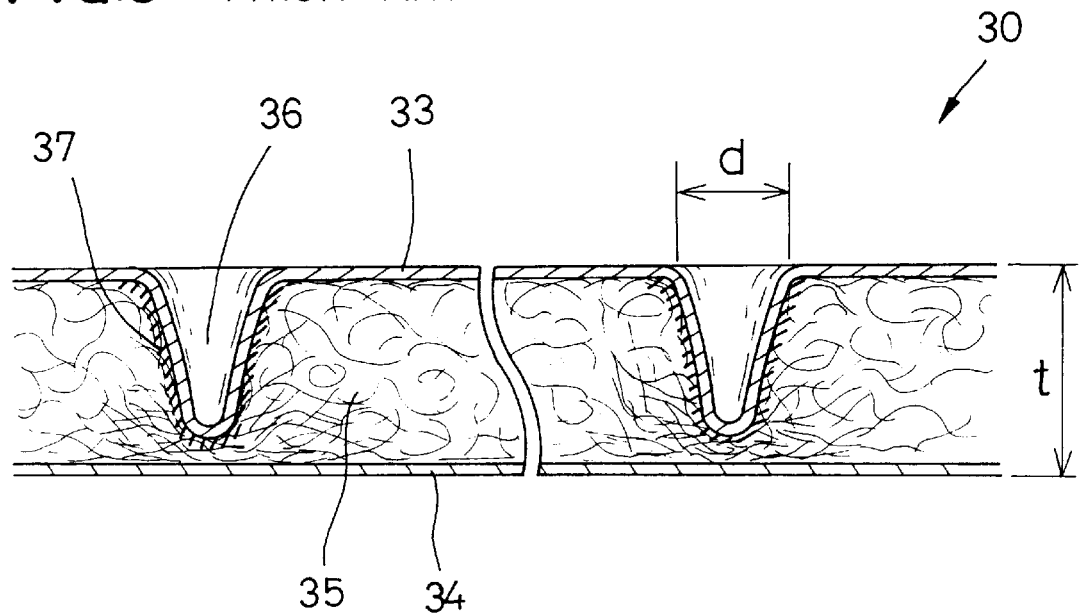
FIG. 3 is a view similar to FIG. 2, showing an important part of a sanitary napkin arranged according to a well known technique.

Most of menstrual discharge flowing into these debossed spots 10 of the napkin 1 permeates the peripheral wall as well as the bottom walls of the enlarged diameter upper depressions 11 and then is absorbed by the core 5. In the reduced diameter lower depressions 12, a quantity of menstrual discharge inevitably stays therein, since they have liquid-impermeable filmy peripheral walls. Nevertheless, the depth $t_2$ as well as the opening diameter $D_2$ of each reduced diameter lower depression 12 may be dimensioned to be less than those in each debossed spot of the conventional absorbent structure 30 as shown by FIG. 3 to decrease the quantity of menstrual discharge which may stay in the reduced diameter lower depression 12. Thereby, an uncomfortable feeling of wetness is alleviated and the presence of menstrual discharge remaining on the napkin 1 becomes inconspicuous to the wearer when she disposes the napkin 1 after use.

EFFECT OF THE INVENTION

The absorbent structure for sanitary article of the invention decreases the quantity of body fluids that remains in the reduced diameter lower depression by dimensioning its opening and depth to be relatively small, since each of the debossed spots at which the topsheet and the liquid-absorbent core are integrated with each other comprises the enlarged diameter upper depression formed by compressing the topsheet and the core together at the spot to be debossed and the reduced diameter lower depression lying inside the enlarged diameter upper depression and formed by partially heating the bottom of the enlarged diameter upper depression under a pressure. With consequence, an uncomfortable feeling of wetness during use of the article can be alleviated and the presence of body fluids remaining on the used article to be disposed can be made as inconspicuous as possible.

What is claimed is:

1. An absorbent structure for a sanitary article including a liquid-absorbent core and a liquid-permeable topsheet made of thermoplastic synthetic fibers with which at least one surface of said core is covered, said core and topsheet being integrated with each other at a plurality of independently and intermittently distributed debossed spots, wherein the improvement comprises:

said debossed spots being individually and separately enclosed depressions relative to each other, each spot having an enlarged diameter upper depression formed by partially compressing said core and said topsheet and a reduced diameter lower depression lying inside said enlarged diameter upper depression and formed by partially depressing a bottom of said enlarged diameter upper depression further into said core and heat-sealing this additionally depressed portion of said bottom of said diameter enlarged upper depression to said core.

2. The absorbent structure for sanitary article according to claim 1, wherein said debossed spots occupy an area of 5 to 25% of a total surface area of said topsheet.

3. The absorbent structure for sanitary article according to claim 1, wherein said topsheet comprises a nonwoven fabric.

4. The absorbent structure for sanitary article according to claim 1, wherein said core contains thermoplastic synthetic fibers up to 20% by weight.

5. The absorbent structure for sanitary article according to claim 1, wherein each of the upper and lower depressions has a thickness of at least 20% of a thickness of said article, and wherein the upper and lower depressions together have a thickness of at least 50% of the thickness of said article.

6. An absorbent structure for sanitary article according to claim 1, wherein the reduced diameter lower depression is located downward from the bottom of said upper depression.

7. The absorbent structure according to claim 6, wherein said bottom of the upper depression is ring shaped and the lower depression extends downward from the center of the ring shape.

8. The absorbent structure according to claim 6, wherein the bottom of the upper depression has an upward facing annular flat surface and the lower depression extends downward from the center of the annular surface.

9. An absorbent structure for a sanitary article including a liquid absorbent core and a liquid permeable topsheet with which at least one surface of the core is covered, said core and topsheet being integrated with each other at a plurality of independent and intermittently distributed debossed spots, wherein the improvement comprises:

said debossed spots being individually and separately enclosed depressions relative to each other, each spot having an enlarged diameter upper depression extending into the topsheet and core and a reduced diameter lower depression lying inside the enlarged diameter upper depression and extending further into said core.

10. The absorbent structure for sanitary article according to claim 1, wherein the upper depression has a diameter in the range of approximately 1 to 15 mm, and wherein the upper depression has a diameter in the range of approximately 0.5 to 3 mm.

* * * * *